United States Patent
Vinjamoori et al.

(10) Patent No.: US 6,809,819 B1
(45) Date of Patent: Oct. 26, 2004

(54) METHODS FOR DETERMINING OIL IN SEEDS

(75) Inventors: Dutt V. Vinjamoori, Chesterfield, MO (US); Pradip K. Das, Olivette, MO (US); John A. Long, Kirkwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 313 days.

(21) Appl. No.: 09/670,085

(22) Filed: Sep. 26, 2000

Related U.S. Application Data

(60) Provisional application No. 60/156,287, filed on Sep. 27, 1999.

(51) Int. Cl.[7] .............................................. G01N 21/00
(52) U.S. Cl. ...................................... 356/337; 356/338
(58) Field of Search ................................ 356/337, 338, 356/339, 341, 928, 947; 210/656, 659; 436/20, 60, 164

(56) References Cited

U.S. PATENT DOCUMENTS

| | | | |
|---|---|---|---|
| 4,980,295 A | * 12/1990 | Udy | ........................... 436/21 |
| 5,670,054 A | 9/1997 | Kibbey et al. | |
| 5,751,421 A | 5/1998 | Wright et al. | |
| 5,776,429 A | 7/1998 | Unger et al. | |
| 5,991,025 A | 11/1999 | Wright et al. | |
| 6,033,646 A | 3/2000 | Unger et al. | |
| 6,077,438 A | 6/2000 | Zambias et al. | |
| 6,122,055 A | 9/2000 | O'Donohue et al. | |
| 6,547,711 B2 | * 4/2003 | Facciotti | ..................... 554/227 |
| 2001/0001575 A1 | * 5/2001 | Anderson et al. | ........... 356/337 |

FOREIGN PATENT DOCUMENTS

| | | |
|---|---|---|
| WO | WO 98/10279 | 3/1998 |

OTHER PUBLICATIONS

International Search Report.

Bergqvist M et al., "Characterization of Honeysuckle (*Lonicera caprifolium* L.) Seed Oil Triacylglycerols by High Performance Liquid Chromatography and Light Scattering Detection" Phytochemical Analysis, vol. 3, 1992, pp 215–217.

Wan et al., "Technology and Solvents for Extracting Oilseeds and Nonpetroleum Oils" US. Champaign, AOCA Press, pp 101–120.

Robutti, "Maize Kernel Hardness Estimation in Breeding by Near–Infrared Transmission Analysis," Analytical Techniques and Instrumentation vol. 72, No. 6, 1995, pp. 632–636.

Archibald et al., "Development of Short–Wavelength Near–Infrared Spectral Imaging for Grain Color Classification," SPIE vol. 3543, 1998, pp. 189–198.

Daun et al., "Comparison of Three Whole Seed Near–Infrared Analyzers for Measuring Quality Components of Canola Seed", vol. 71, No. 10, 1994, pp. 1063–1068.

Bertrand Matthäus and Ludger Brühl, "Comparison of Different Methods for the Determination of the Oil Content in Oilseeds", JAOCS, vol. 78, No. 1 (2001), pp. 95–102.

Fernando Tobalina Bonis, "Detectores evaporativos de Light Scattering: la herramienta ideal para el análisis de triglicéridos por HPLC" (Evaporative Light scattering detectors: and ideal tool for HPLC analysis of triglycerides), Sugelabor, S.A., Tech. Lab. (2000); ISSN: 0371–5728.

(List continued on next page.)

*Primary Examiner*—Rodney Fuller
(74) *Attorney, Agent, or Firm*—Joseph A. Schaper

(57) ABSTRACT

The present invention relates to methods for analyzing agricultural products. More particularly, the present invention relates to methods for analysis of the oil content of one or more seeds.

81 Claims, 8 Drawing Sheets

OTHER PUBLICATIONS

M. F. Caboni, L. S. Conte and G. Lercker, "Rapid HPLC Analysis of Troiacylglycerols by Isocratic Elution and Light Scattering Detection", Ital. J. Food Sci. No. 2, 1992, pp. 125 132.

Priya Ranjan Kumar and Kenshiro Fujimoto, "A Simple Method for Determination of Oil Content of Seed and Its Fatty Acid Composition by GLC Using Small Amount of Sample", Faculty of Agriculture, Tohoku University, 1977; CAN 86:104535, pp. 41–42.

Dowell et al., "Automated Single Wheat Kernel Quality Measurement Using Near–Infrared Reflectance," ASAE Annual International Meeting, 1997, paper No. 973022.

Delwiche, "Single Wheat Kernel Analysis by Near–Infrared Transmittance: Protein Content," Analytical Techniques and Instrumentation, vol. 72, No. 1, 1995, pp. 11–16.

Dowell, "Automated Color Classification of Single Wheat Kernels Using Visible and Near–Infrared Reflectance," Cereal Chemistry, vol. 75(1), 1998, pp. 142–144.

Massie and Norris, "Spectral Reflectance and Transmittance Properties of Grain in the Visible and near Infrared", Transactions of the ASAE, Winter Meeting of the American Society of Agricultural Engineers, 1965, pp. 598–600.

Orman and Schumann, "Comparison of Near–Infrared Spectroscopy Calibration Methods for the Prediction of Protein, Oil, and Starch in Maize Grain," J. Agric. Food Chem. vol. 39, 1991, pp. 883–886.

Velasco et al., "Estimation of seed weight, oil content and fatty acid composition in intact single seeds of rapeseed (*Brassica napus* L.) by near–infrared reflectance spectroscopy," Euphytica vol. 106, 1999, pp. 79–85.

Taylor et al., "Determination of Oil Content in Oilseeds by Analytical Supercritical Fluid Extraction," JAOCS, vol. 70, No. 4, 1993, pp. 437–439.

Robertson et al., "Analysis of Oil Content of Sunflower Seed by Wide–Line NMR," Journal of the American Oil Chemists' Society, vol. 56, No. 7, 1976, pp. 961–964.

Macrae et al., "Analysis of carbohydrates using the mass detector," Journal of Chromatography, vol. 210, 1981, pp. 138–145.

Schaefer et al., "Determination of Oil, Starch, and Protein Content of Viable Intact Seeds by Carbon–13 Nuclear Magnetic Resonance," Journal of the American Oil Chemists' Society, vol. 51, No. 12, 1974, pp. 562–563.

Charlesworth, "Evaporative Analyzer as a Mass Detector for Liquid Chromatography," Analytical Chemistry, vol. 50, No. 11, 1978, pp. 1414–1420.

* cited by examiner

CORRELATION OF LS RESULTS WITH ASE FOR SOY

| SAMPLE | % OIL LS | % OIL ASE | LS/ASE |
|---|---|---|---|
| 1 | 17.7 | 19.7 | 0.90 |
| 2 | 19.7 | 21.8 | 0.90 |
| 3 | 17.8 | 20.1 | 0.89 |
| 4 | 19.4 | 21.8 | 0.89 |
| 5 | 18.8 | 23.3 | 0.81 |
| 6 | 18.3 | 21.9 | 0.84 |
| 7 | 16.9 | 20.1 | 0.84 |
| 8 | 19.3 | 22.2 | 0.87 |
| 9 | 17.8 | 20.5 | 0.87 |
| 10 | 17.9 | 20.6 | 0.87 |
| 11 | 20.6 | 18.3 | 1.13 |
| 12 | 18.6 | 20.5 | 0.91 |

FIG. 4

METHODS FOR DETERMINING OIL IN SEEDS

CROSS-REFERENCE TO RELATED APPLICATION

This application claims priority to Provisional Patent Application U.S. Ser. No. 60/156,287 entitled "Method for Determining Total Oil in Seeds," which was filed Sep. 27, 1999.

FIELD OF THE INVENTION

The present invention relates to methods for analyzing agricultural products. More particularly, the present invention relates to methods for analysis of the oil content of one or more seeds.

BACKGROUND OF THE INVENTION

The improvement of techniques used for analysis of agricultural products for desired traits has long been a goal. Several methods have conventionally been used to analyze a sample for the presence of a specific trait. Quantitation of oil content of seeds is often performed with conventional methods, such as near infrared analysis (NIR), nuclear magnetic resonance imaging (NMR), soxhlet extraction, accelerated solvent extraction (ASE), microwave extraction, and super critical fluid extraction. These conventional methods, however, are often not able to accurately discern the relative or absolute levels of oil in very small seed samples.

During the past decade, near infrared (NIR) spectroscopy has become a standard method for screening seed samples whenever the sample of interest has been amenable to this technique. Samples studied include wheat, maize, soybean, canola, rice, alfalfa, oat, and others (see, for example, Massie and Norris, "Spectral Reflectance and Transmittance Properties of Grain in the Visible and Near Infrared", Transactions of the ASAE, Winter Meeting of the American society of Agricultural Engineers, 1965, pp. 598–600, Archibald et al. "Development of Short-Wavelength Near-Infrared spectral Imaging for Grain Color Classification," SPIE Vol. 3543, 1998, pp. 189–198, Delwiche, "Single Wheat Kernel Analysis by Near-Infrared Transmittance: Protein Content," Analytical Techniques and Instrumentation, Vol. 72, 1995, pp. 11–16, Dowell, "Automated Color Classification of Single Wheat Kernels Using Visible and Near-Infrared Reflectance," Vol. 75(1), 1998, pp.142–144, Orman and Schumann, "Comparison of Near-Infrared Spectroscopy Calibration Methods for the Prediction of Protein, Oil, and Starch in Maize Grain," Vol. 39, 1991, pp.883–886, Robutti, "Maize Kernel Hardness Estimation in Breeding by Near-Infrared Transmission Analysis," Vol. 72(6), 1995, pp.632–636, U.S. Pat. No. 5,991,025 to Wright et al., U.S. Pat. No. 5,751,421 to Wright et al., Daun et al., "Comparison of Three whole Seed Near-Infrared Analyzers for Measuring Quality Components of Canola Seed", Vol. 71, no. 10, 1994, pp.1063–1068, all of which are herein incorporated by reference in their entirety).

NIR analysis of single seeds has been reported (see Velasco, et al., "Estimation of Seed Weight, Oil Content and Fatty Acid Composition in Intact Single Seeds of Rapeseed (*Brassica napus L.*) by Rear-Infrared Reflectance Spectroscopy," Euphytica, Vol. 106, 1999, pp.79–85, Delwiche, "Single Wheat Kernel Analysis by Near-Infrared Transmittance: Protein Content," Analytical Techniques and Instrumentation, Vol. 72, 1995, pp. 11–16, Dowell, "Automated Color Classification of Single Wheat Kernels Using Visible and Near-Infrared Reflectance," Vol. 75(1), 1998, pp.142–144, Dowell et al., "Automated Single Wheat Kernel Quality Measurement Using Near-Infrared Reflectance," ASAE Annual International Meeting, 1997, paper number 973022, all of which are herein incorporated by reference in their entirety). These methods, however, are not sensitive enough to accurately determine the oil content of very small seeds, which limits their use. NMR has also been used to analyze oil content in seeds (see, for example, Robertson and Morrison, "Analysis of Oil Content of Sunflower Seed by Wide-Line NMR," Journal of the American Oil Chemists Society, 1979, Vol. 56, 1979, pp. 961–964, which is herein incorporated by reference in its entirety). However, this non-destructive technique is also often not suitable for the analysis of seed oil when the seed of interest is small.

Other techniques, including soxhlet extraction, accelerated solvent extraction (ASE), microwave extraction, and super critical fluid extraction, that are conventionally used to determine oil content use gravimetry as the final measurement step (see, for example, Taylor et al., "Determination of Oil Content in Oilseeds by Analytical Supercritical Fluid Extraction," Vol. 70 (no. 4), 1993, pp. 437–439, which is herein incorporated by reference in its entirety). Gravimetry, however, is not suitable for use with small samples, including small seeds and seed with little oil content, because oil levels in these samples can be below the level of minimum sensitivity for the technique. Further, the use of gravimetry is time consuming and is not amenable to high-throughput automation.

Needed in the art are methods for rapid and accurate analysis of seed samples, and particularly small seed samples, that can be used to efficiently analyze the oil content of individual seeds and that are amenable to automation. The present invention provides such methods.

SUMMARY OF THE INVENTION

The present invention includes and provides a method for determining oil content of a seed comprising: extracting oil from a seed using a solvent; evaporating the solvent in a stream of gas to form oil particles; directing light into the stream of gas and the oil particles, thereby forming reflected light; detecting the reflected light; and, determining the oil content based on the reflected light.

The present invention includes and provides a method for determining oil content of a seed comprising extracting oil from a seed using a solvent; separating the solvent from the seed; evaporating the solvent in a stream of gas to form oil particles; directing light into the stream of gas and the oil particles, thereby forming reflected light; detecting the reflected light; and, determining the oil content based on the reflected light.

The present invention includes and provides a method for determining oil content of a seed comprising: disrupting the seed to produce ground seed; extracting oil from the ground seed using a solvent; evaporating the solvent in a stream of gas to form oil particles; directing light into the stream of gas and the oil particles, thereby forming reflected light; detecting the reflected light; determining the oil content based on the reflected light.

The present invention includes and provides a method for determining oil content of an agricultural material, comprising: extracting oil from the material using a solvent; evaporating the solvent in a stream of gas to form oil particles; directing light into the stream of gas and the oil particles, thereby forming reflected light; detecting the reflected light; and, determining the oil content based on the reflected light.

All The present invention includes and provides a method for determining oil content of a batch seed sample, comprising: extracting oil from the batch seed sample using a solvent; evaporating the solvent in a stream of gas to form oil particles; directing light into the stream of gas and the oil particles, thereby forming reflected light; detecting the reflected light; and, determining the oil content based on the reflected light.

The present invention includes and provides a method for selecting a seed having an enhanced oil content, comprising: extracting oil from a seed using a solvent; evaporating the solvent in a stream of gas to form oil particles; directing light into the stream of gas and the oil particles, thereby forming reflected light; detecting the reflected light; determining the oil content based on the reflected light; and, selecting a seed with a similar genetic background to the seed based on the oil content.

The present invention includes and provides a method of introgressing a trait into a plant comprising: extracting oil from a seed using a solvent; evaporating the solvent in a stream of gas to form oil particles; directing light into the stream of gas and the oil particles, thereby forming reflected light; detecting the reflected light; determining the oil content based on the reflected light; selecting a seed with a similar genetic background to the seed based on the oil content; growing a fertile plant from the related seed; and, utilizing the fertile plant as either a female parent or a male parent in a cross with a second plant.

The present invention includes and provides a method for determining oil content of a seed comprising: extracting oil from a seed using a solvent; nebulizing the solvent and the oil under high pressure into a device capable of evaporating the solvent; evaporating the solvent in a stream of gas in the device to form oil particles; directing light into the stream of gas and the oil particles, thereby forming reflected light; detecting the reflected light; determining the oil content based on the reflected light.

The present invention includes and provides a method for selecting a seed having an enhanced oil content, comprising: a) extracting oil from a seed using a solvent; b) evaporating the solvent in a stream of gas to form oil particles; c) directing light into the stream of gas and the oil particles, thereby forming reflected light; d) detecting the reflected light; e) determining the oil content based on the reflected light; f) repeating steps a) through e) one or more times, and, g) selecting one or more seeds based on the oil content.

DESCRIPTION OF THE FIGURES

FIG. 4 is a table that compares the results of the present invention with the conventional technique of accelerated solvent extraction for soybean.

DETAILED DESCRIPTION OF THE INVENTION

Analytical Methods

Figure 1:
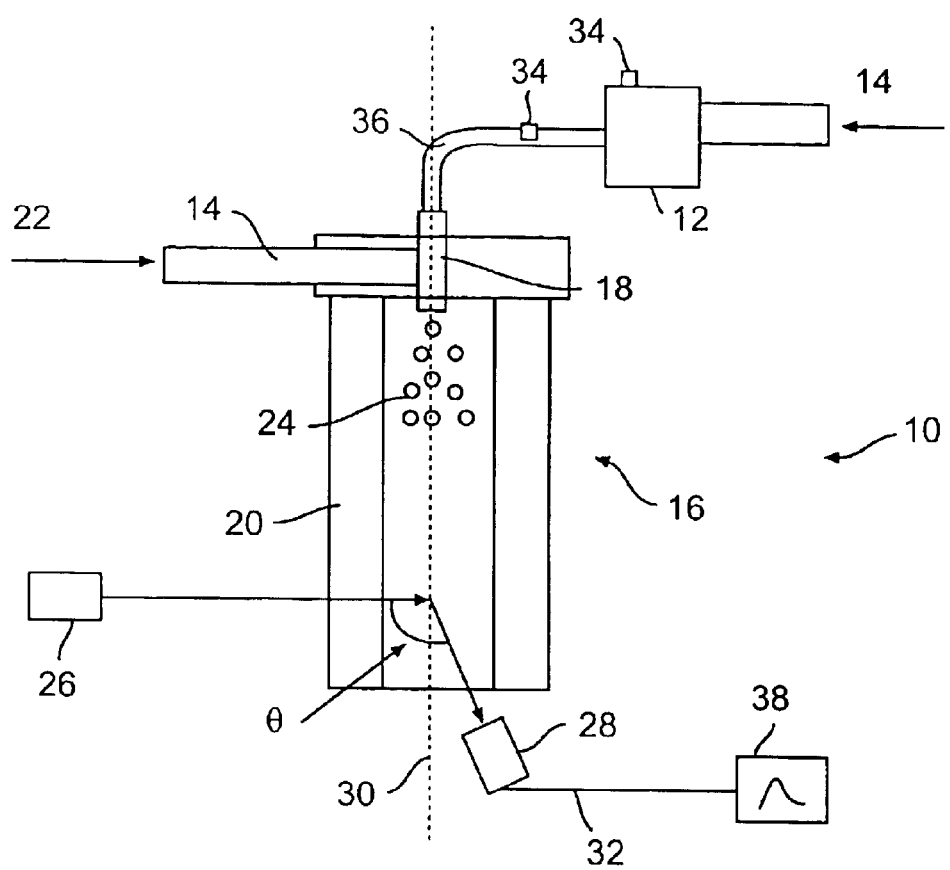
FIG. 1 is a schematic diagram of a cross section of one embodiment of a system that is capable of carrying out the methods of the present invention.
Figure 2:
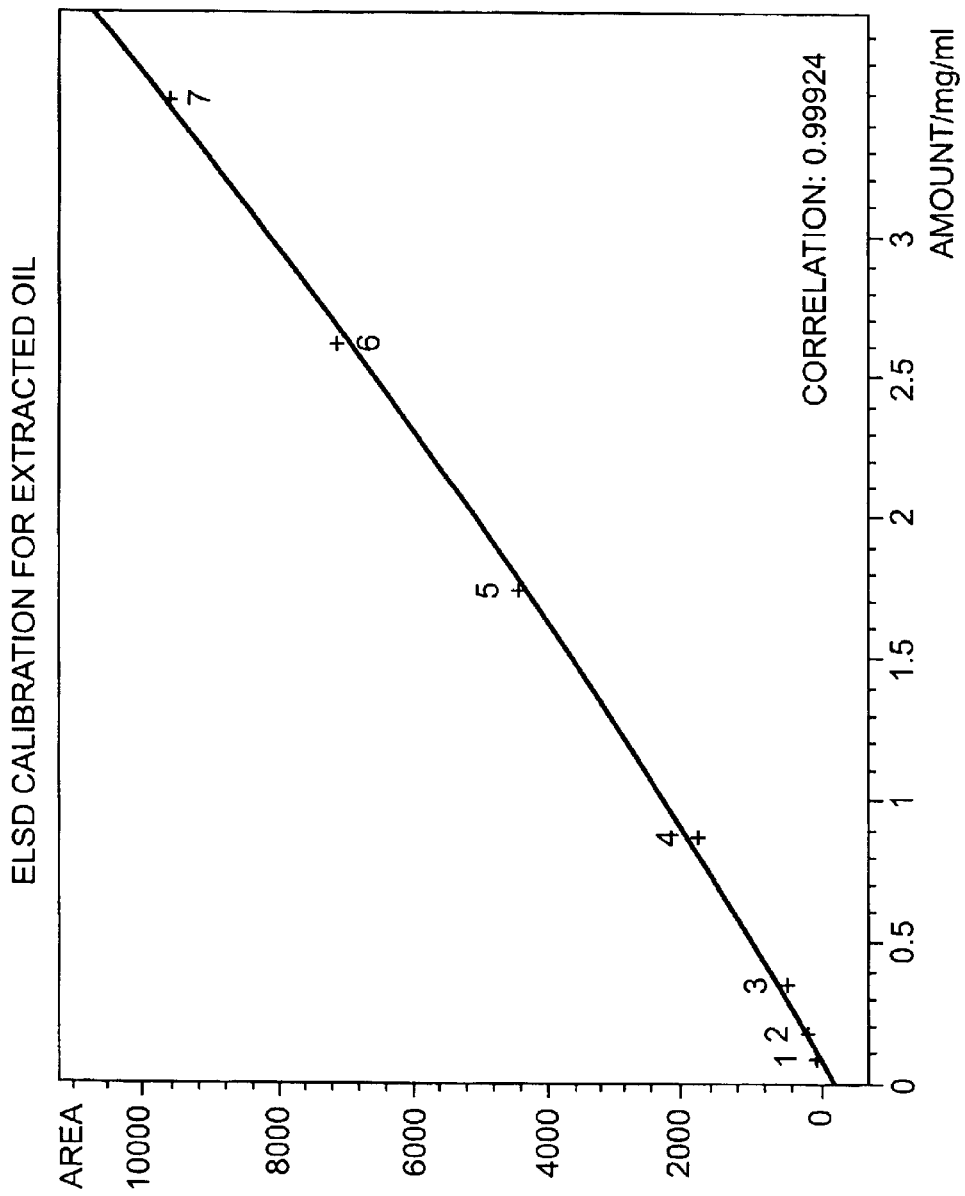
FIG. 2 is plot showing a calibration curve for oil content.
Figure 3:
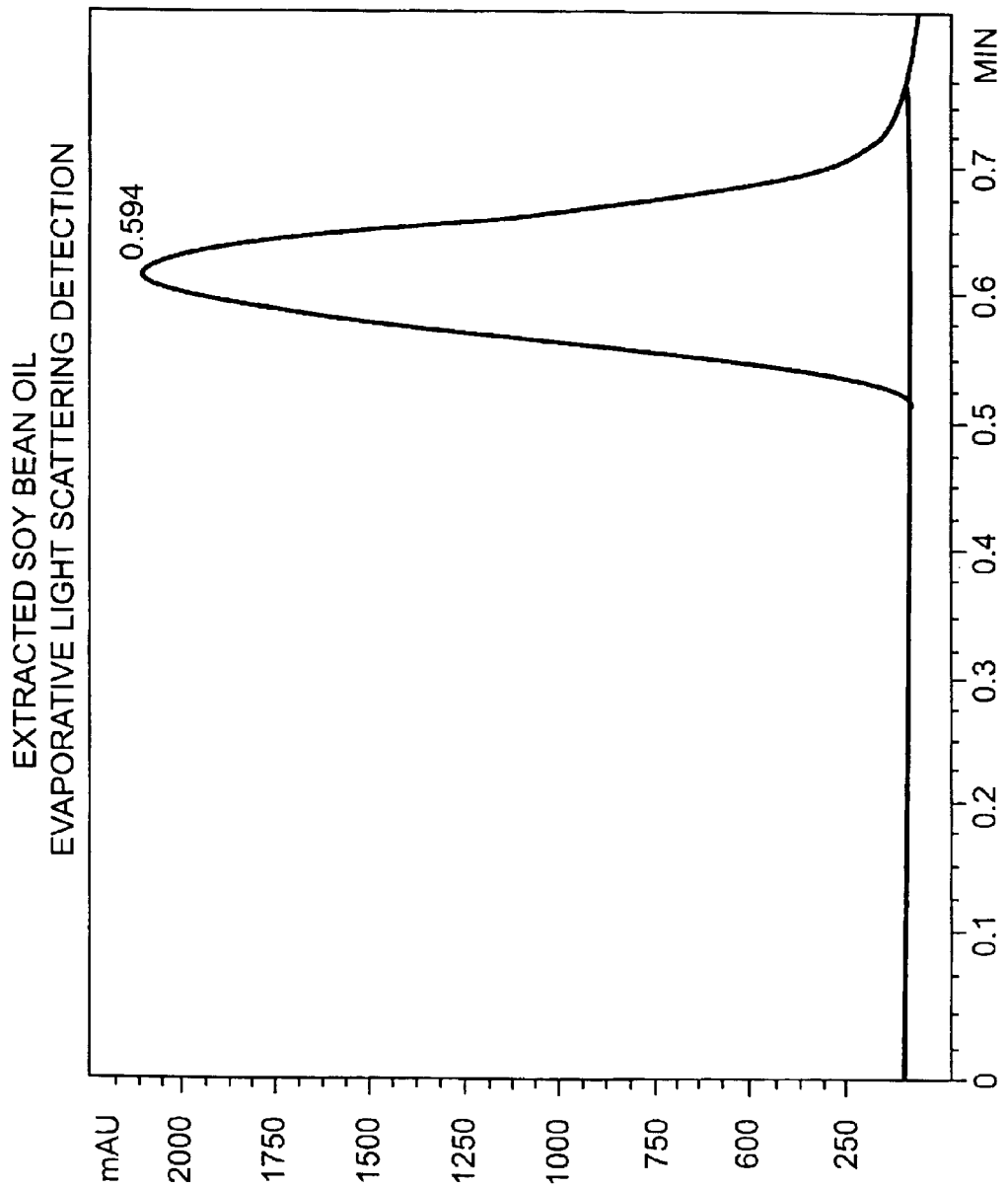
FIG. 3 is a chromatograph of extracted soybean oil content.
Figure 5:
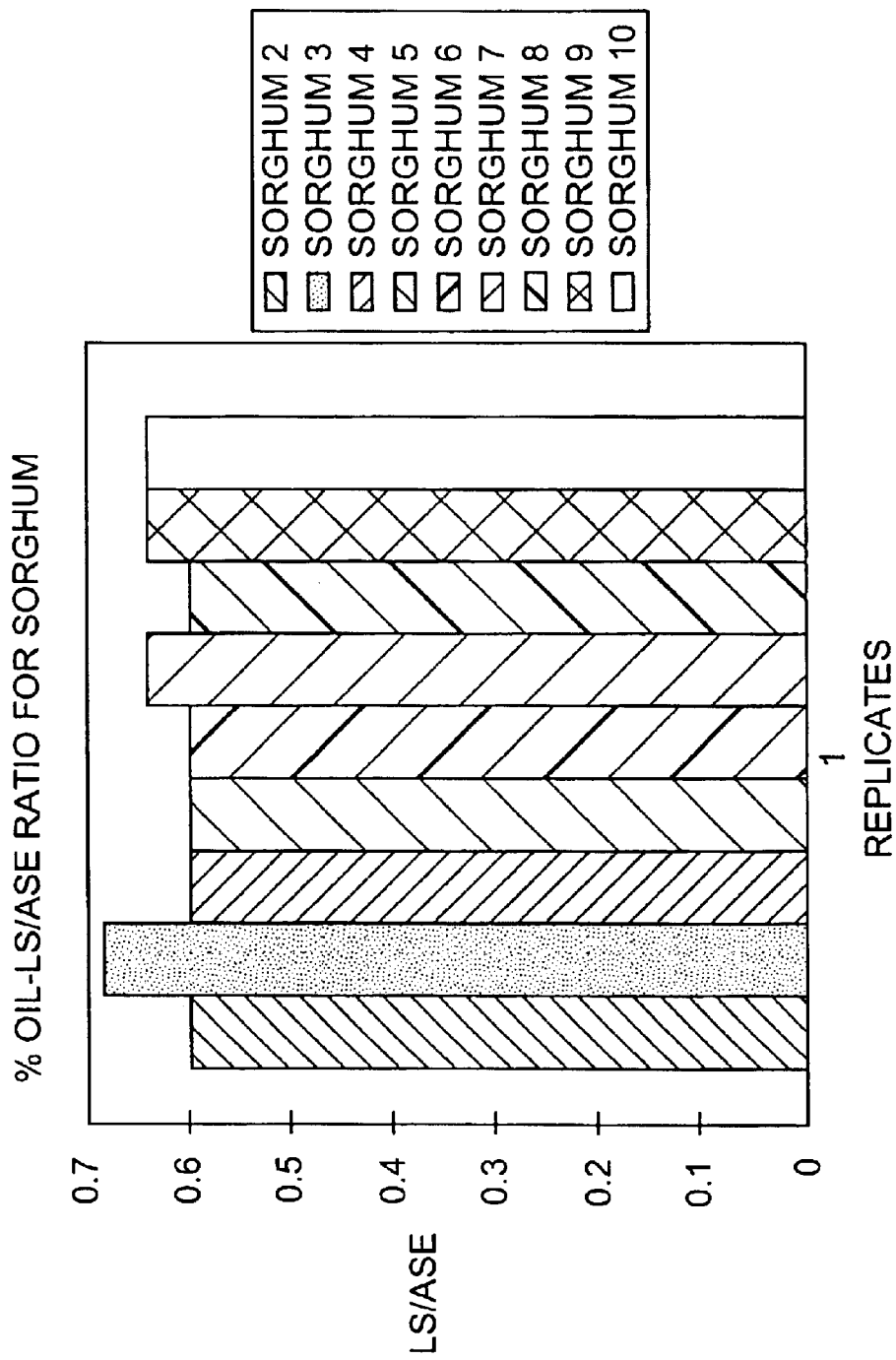
FIG. 5 is a graph that compares the results of the present invention with the conventional technique of accelerated solvent extraction for sorghum.
Figure 6:
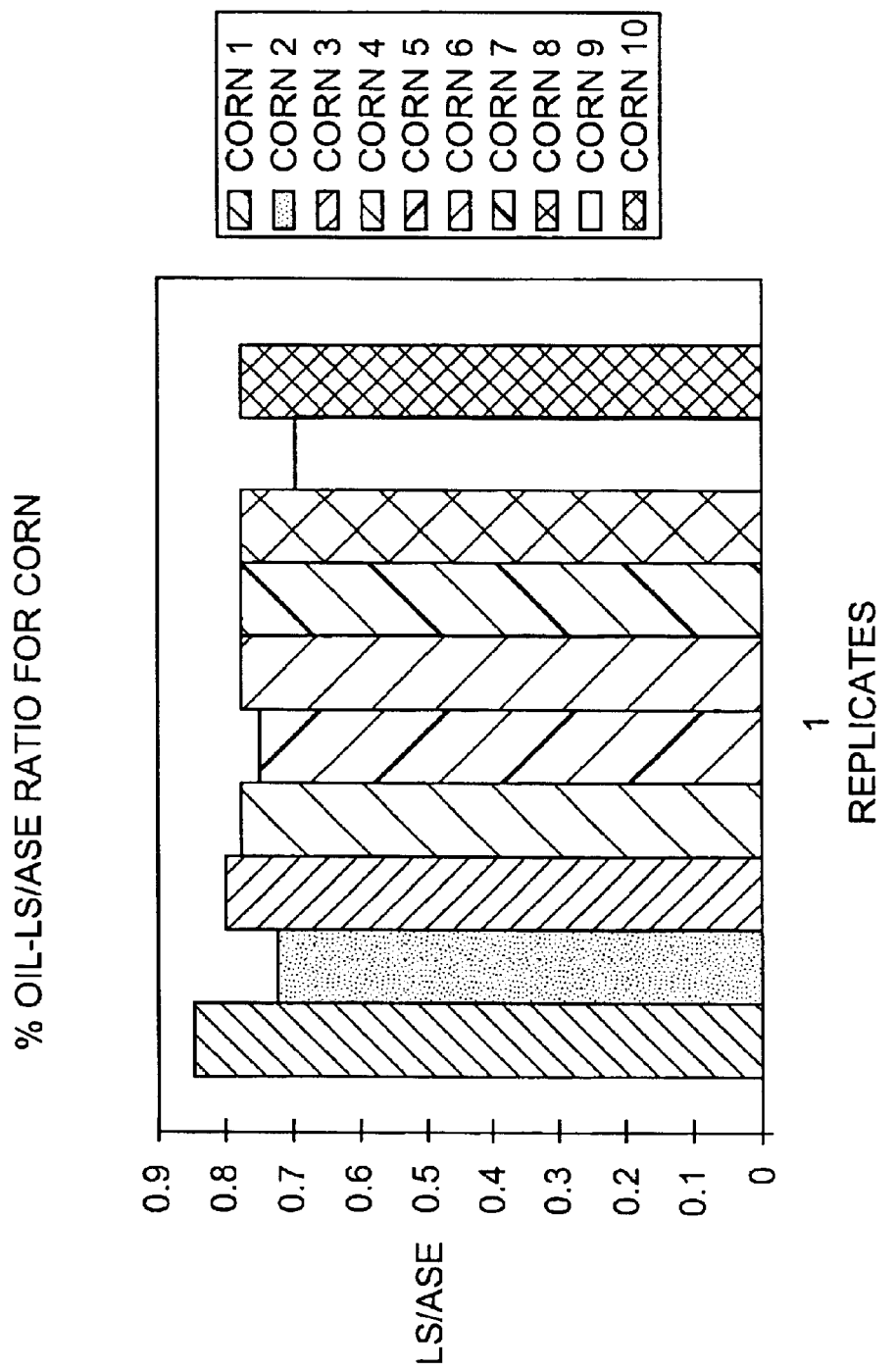
FIG. 6 is graph that compares the results of the present invention with the conventional technique of accelerated solvent extraction for maize.
Figure 7:
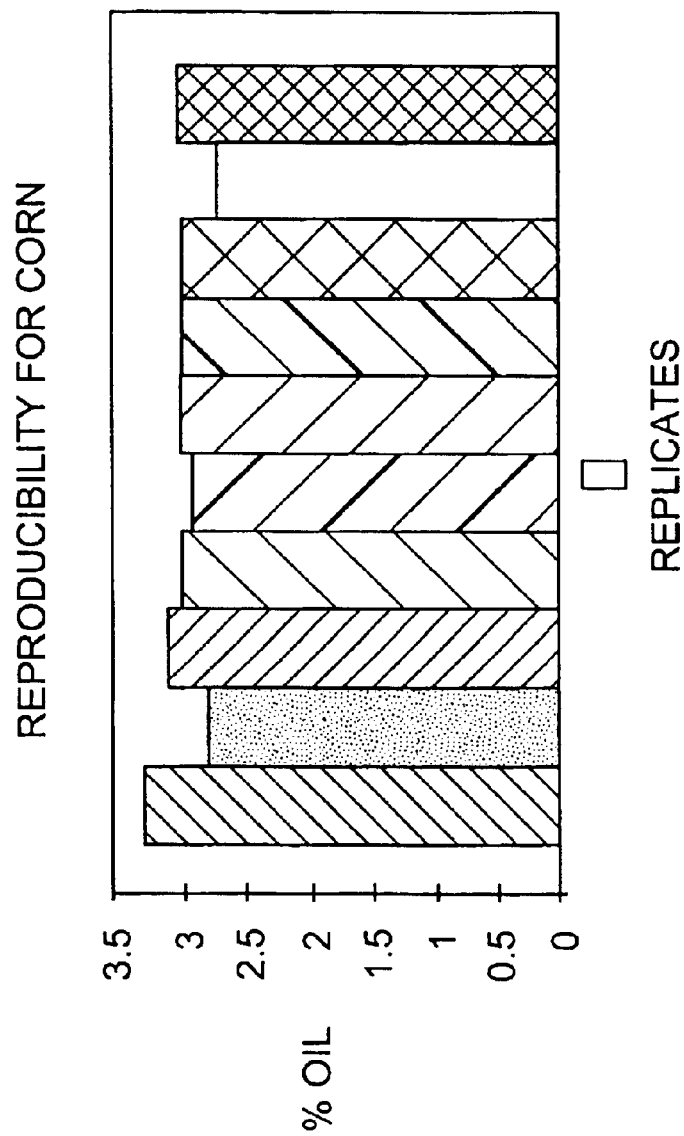
FIG. 7 is a graph showing the reproducibility of one embodiment of the present invention for maize.
Figure 8:
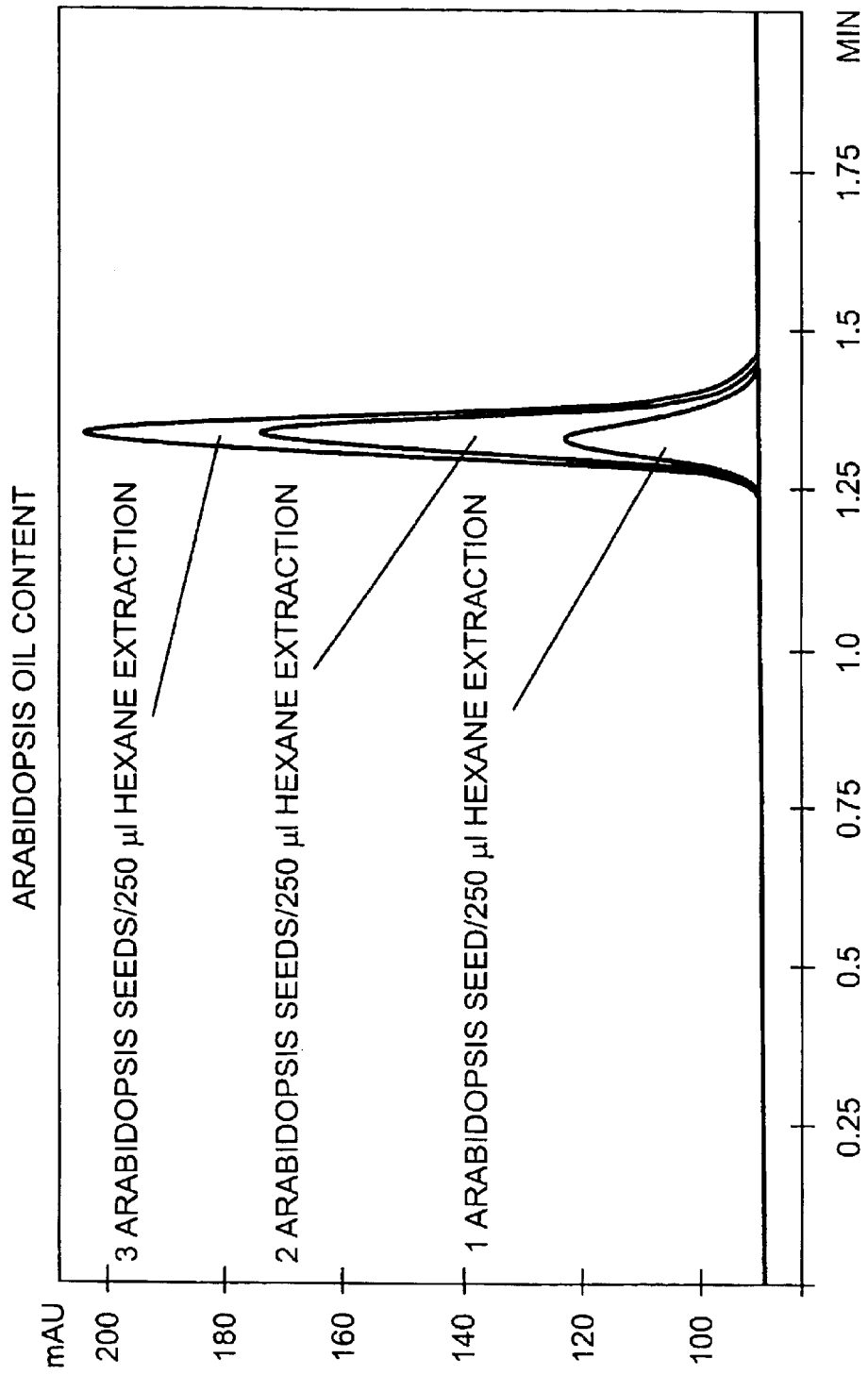
FIG. 8 is a overlayed chromatograph showing oil content determination for one, two, and three *Arabidopsis thaliana* seeds.

The present invention provides analytical methods for selecting seeds having a desired oil content. In one embodiment, the present invention is a method for determining oil content of a single seed comprising: extracting oil from a single seed using a solvent; evaporating the solvent in a stream of gas to form oil particles; directing light into the stream of gas and the oil particles, thereby forming reflected light; detecting the reflected light; and, determining the oil content based on the reflected light.

In a preferred embodiment, all fractions of oil of a sample are extracted. In another preferred embodiment, triglycerides are used as a marker for the total oil content. In this embodiment, the signals produced by light scattering detection are derived predominantly from the triglyceride fraction of the total oil content.

The extracted oil can then be separated from solids in a centrifuge. To determine oil content, the supernatant can be injected into a device that is capable of providing a stream of gas in which the solvent can evaporate, and the mass of the remaining oil can be determined with an evaporative light scattering detector.

As used herein "oil content" refers to the amount of oil present in a sample or particular fraction or fractions of oil, e.g. 5 nanograms (ng) per seed of total oil, 5 ng total oil per 10 grams of dry weight of tissue, or 5 ng of triglycerides per seed, or 5 ng of triglycerides per 10 grams of dry weight of tissue. Particularly preferred fractions of oil include, without limitation, triglycerides, free fatty acids, waxes, phospholipids, phytosterols, and tocopherols. In a preferred embodiment the fraction comprises triglycerides. As used herein, "composition" refers to biochemical constituents of an agricultural sample, for example, the ratio of triglycerides to total oil content. As used herein, "sample" means any part of one or more plants being analyzed, including, for example, a portion of a seed, a single seed, more than one seed, a part of one or more plants other than seeds, any plant tissue, agricultural material, or any combination thereof. A sample can be in any form, including whole seeds, intact plant tissue, whole agricultural material, and any disrupted form of any of these.

Any seed can be utilized in a method of the present invention. In a preferred embodiment, the seed is selected from the group consisting of alfalfa seed, apple seed, *Arabidopsis thaliana* seed, banana seed, barley seed, bean seed, broccoli seed, castorbean seed, citrus seed, clover seed, coconut seed, coffee seed, maize seed, cotton seed, cucumber seed, Douglas fir seed, Eucalyptus seed, Loblolly pine seed, linseed seed, melon seed, oat seed, olive seed, palm seed, pea seed, peanut seed, pepper seed, poplar seed, Radiata pine seed, rapeseed seed, rice seed, rye seed, sorghum seed, Southern pine seed, soybean seed, strawberry seed, sugarbeet seed, sugarcane seed, sunflower seed, sweetgum seed, tea seed, tobacco seed, tomato seed, turf, and wheat seed. In a more preferred embodiment, the seed is selected from the group consisting of cotton seed, *Arabidopsis thaliana* seed, maize seed, soybean seed, rapeseed seed, rice seed, and wheat seed. In an even more preferred embodiment, the seed is a rapeseed seed. In another even more preferred embodiment, the seed is an *Arabidopsis thaliana* seed. In another even more preferred embodiment, the seed is a soybean seed. In yet another even more preferred embodiment, the seed is a maize seed.

Further, any portion of any of the above-mentioned seeds can be utilized. For example, any of the above-mentioned seeds can be subdivided for the purposes of analysis. A seed can, for example, be divided so as to bisect the germ and endosperm in order to allow for parallel testing and planting of the two halves. A seed can further be divided by tissue type. In a preferred embodiment, a sample can comprise endosperm that has been mechanically separated from the germ tissue in order to analyze the germ or the endosperm for oil content using a method of the present invention.

Other plant tissues or agricultural materials can be substituted, without limitation, for seeds as the sample. As used herein, plant tissues include, without limitation, any plant part such as leaf, flower, root, petal. As used herein, agricultural materials include, without limitation, plant tissues such as seeds, but also include, without limitation, non-plant based material such as non-organic matter or non-plant based matter that occur in an agricultural context. Fungal samples are an example of an agricultural material.

Individual seeds or batches of seeds can be utilized with the methods of the present invention. A batch of seeds is any number of seeds greater than one. As used herein, a "member" of a batch is any single seed within the batch. A batch of seeds can be defined by number. In an embodiment, a batch of seeds is greater than 10,000, 5,000, 2,500, 1,000, 100, 20, 10, 5, 4, or 3 seeds. In another embodiment a batch comprises between 5,000 and 10,000 seeds, between 1,000 and 5,000 seeds, 100 and 2,500 seeds, 100 and 1,000 seeds, 10 and 100 seeds, 10 and 20 seeds, 5 and 10 seeds, 1 and 5 seeds, 1 and 4 seeds, and 1 and 3 seeds. In another embodiment the batch of seeds may be classified by its origin, such as seeds that are derived from a single ear, single plant, or single plant cross.

In one embodiment, the seeds from a single source are provided together for analysis. In another embodiment the single source can be any source that provides seeds having a similar genetic background, such as an ear of maize, a single plant, or the product of a single cross. If a seed or a batch of seeds is entirely consumed by a method of the present invention, then seeds having a common genetic background can be used to propagate a desired trait found in an analyzed seed.

As used herein, a seed with a similar genetic background to a first seed is a seed that shares at least 25%, more preferably 50%, even more preferably 75% or 100% of the genetic background of the first seed. For example, the progeny of a cross between two plants shares 50% of its genetic background with each parent to the cross.

The mass of a sample can be any mass that yields a measurable result. In a preferred embodiment, the sample mass is less mass than 1,000 grams, more preferably less than 500, 100, 50, 25, 10, 5, and 1 gram. In another preferred embodiment, the sample is one seed.

In order to determine the oil content of a sample, the oil is extracted from the sample. Extraction can be performed on the sample using a suitable solvent. The solvent can be any solvent that is capable of extracting oil from the sample without also extracting unwanted impurities from the sample. In a preferred embodiment, the solvent is any non-polar solvent. In a further preferred embodiment, the solvent is selected from the group consisting of hexane, decane, petroleum ether, an alcohol, or acetonitirile. In a preferred embodiment the solvent comprises isopropanol. In a more preferred embodiment, the solvent comprises hexane.

The amount of solvent used will depend upon the amount of sample analyzed. The volume of solvent sufficient to extract a detectable amount of oil is known in the art. In a preferred embodiment, sufficient solvent is used to extract all available oil from the sample. The available oil in a sample can be the total oil in the sample, or any amount less than the total amount of oil. In another embodiment, 0.1 to 100 milliliters of solvent is used for every milligram of sample being analyzed, with 0.2 to 50 milliliters of solvent per milligram of sample preferred, 0.25 to 10 milliliters of solvent per milligram of sample more preferred, and 0.5 to 3 milliliters of solvent per milligram especially preferred.

As used herein, "extracting oil" from a sample means disposing the sample in contact with a solvent in order to transfer oil from the sample to the solvent. During extraction, a sample can be exposed to the solvent in any manner that transfers a detectable amount of oil from the sample to the solvent. A sample can, for example, be added to an appropriate volume of solvent in an intact state. Oil then is drawn from the intact sample to the solvent. In one embodiment, the oil is held in solution in the solvent.

In order to increase the rate of oil transfer or the amount of oil that is transferred during extraction, a sample can be disrupted. As used herein, "disrupting" a sample means physically altering a sample in order to increase the surface area of the sample that can be exposed to a solvent. Disrupting can be performed with any suitable device, including devices for grinding, milling, crushing, cutting, and pulverizing, among others. A Tecator Cyclotec 1093 Sample Mill (Fos Tecator, P.O. Box 70, S-26321 Hoeganaes, Sweden) is one example of a commercially available milling device.

In order to increase the rate of oil transfer or the amount of oil transferred during extraction, the combined sample and solvent mixture can be agitated. As used herein, "agitating" a solvent and sample means using any technique to increase the physical interaction of the solvent and sample. Agitation of the solvent and sample can be performed, for example, with vibrators, agitators, rotating wheels, and shakers, among others. One example of an agitation device is a Glas-Col rotating wheel (Glas-Col Apparatus Co, 711 Hulman Street, P O Box 2128, Terre Haute, Ind. 47802-0128 USA). Additionally, the temperature of the solvent and the sample can be increased in order to improve the rate of oil transfer or the amount of oil transferred.

The amount of disrupting and agitating of a sample will depend on the desired result of the analysis. In some instances it will be desirable to compare the relative oil content of two or more samples. In these instances, it is unnecessary to extract the total oil content from the sample. Instead, a portion of the total oil content can be extracted from each sample and the amounts can be compared to determine the relative oil content of the samples. In one embodiment, in order to determine relative oil content, disruption and agitation of samples can be minimal. For example, multiple samples can be disposed in solvent without disrupting the sample beforehand, and then agitated. After centrifugation and evaporative light scattering detection, the relative oil content of the samples can be ascertained.

In another embodiment, a quantitative estimation of total oil content is obtained by disrupting a sample and agitating the sample in solvent in order to transfer almost all of the oil from the sample to the solvent. The extent to which a sample will need to be disrupted and agitated in order to liberate all of the oil content depends on the type of sample under analysis and is known in the art.

In a preferred embodiment, a sample is ground for between 0.1 and 5 minutes in a sample mill, and more preferably between 0.5 and 3 minutes. In another embodiment, a sample is agitated for between 0.5 and 20 minutes, more preferably between 1 and 15 minutes, and even more preferably from 3 to 8 minutes.

After extraction, the solvent and extracted oil, which is in solution in the solvent, can be further separated from the remaining sample in order to improve the uniformity of the composition of the solvent and extracted oil. Any device and method for separating solids from a solution can be used if the resulting solvent comprises an amount of non-oil impurities that does not significantly affect detection of oil in later steps. One example of a suitable centrifuge is a Fisher Model 235B Micro-Centrifuge (Fisher Scientific, 4500 Turnberry Dr., Hanover Park, Ill. 60103). As used herein, "separating" solvent from seed means removing the solvent containing the extracted oil from the remainder of the sample. Separation can be performed, for example, with any conventional technique, including filtration, settling, and centrifugation. In a preferred embodiment, after extraction the solvent and sample solids are centrifuged. Centrifugation causes the solids to sediment and form a pellet, from which the solvent is separated as supernatant. The supernatant can then be siphoned off of the pellet to complete the separation. In a preferred embodiment, the sample and solvent are centrifuged for between 0.1 to 5 minutes, more preferably for between 0.5 and 3 minutes, and even more preferably for between 0.75 and 2 minutes.

After extraction of the oil from the solvent, the oil content in the solvent can be determined using evaporative light scattering detection methods. Any device that is capable of providing a stream of gas in which the solvent can evaporate and form oil particles in solvent vapor can be used in conjunction with a light source capable of producing light that is reflected by the oil particles and a light detector capable of detecting the reflected light.

As used herein, "evaporating solvent" means causing the solvent in the solvent and oil solution to go to a gaseous vapor phase from a liquid phase, while maintaining the oil in a liquid phase. Evaporation of the solvent results in free oil particles, or droplets, that can then be passed through a light source and light detector for determination of the mass of the oil. Evaporation of the solvent can be carried out in any device that is capable of providing a stream of gas in which the solvent can evaporate. As used herein, a "stream of gas" is a continuous flow of gas in which a solvent can be evaporated. The gas used in the stream of gas can be any gas into which the solvent can evaporate. In one embodiment, the gas is an inert or noble gas. In another embodiment, the gas is selected from the group consisting of nitrogen, inert or noble gases, and carbon dioxide and mixtures thereof. In another preferred embodiment, the gas used in the stream of gas comprises nitrogen. In yet another preferred embodiment, the gas used comprises nitrogen of at least 99% purity.

The device that is capable of providing a stream of gas in which the solvent can evaporate can be any conventional device used for evaporative light scattering detection. In one embodiment, the device is a tube that is affixed at one end to a different device for supplying the solvent at a controllable rate. Such a tube can be a "drift" tube as are known in the art. The tube can have any geometry that allows for the evaporation of the solvent, with an approximately cylindrical geometry preferred. At one end of the tube, a device for introducing the solvent at a controlled rate into the tube is provided.

The rate at which the stream of gas flows can be any rate that allows for sufficient evaporation of a solvent in a stream of gas. The rate at which the stream of gas flows will depend on which solvent and gas are used, the relative amounts of each, the temperature of each, and the time of contact of the two. In a preferred embodiment, the flow rate of gas in the tube is between 0.5 and 20 liters per minute, more preferably between 1 and 10 liters per minute, and even more preferably between 1.5 and 5 liters per minute. In a preferred embodiment, the solvent is introduced into the stream at a rate between 0.1 and 10 milliliters per minute, more preferably between 0.2 and 5 milliliters per minute, and even more preferably between 0.3 and 5 milliliters per minute. In a preferred embodiment the temperature of the solvent is between 20 and 100 degrees Celsius, more preferably between 30 and 75 degrees Celsius, and even more preferably between 30 and 50 degrees Celsius. In a preferred embodiment the tube is maintained at a temperature between 20 and 200 degrees Celsius, more preferably between 50 and 150 degrees Celsius, and even more preferably between 80 and 120 degrees Celsius.

The solvent can be introduced into a device that is capable of providing a stream of gas in which the solvent can evaporate in any manner and with any device for introducing the solvent at a controlled rate. Devices that allow for the delivery of a constant volume of solvent over time include any device for introducing the solvent at a controlled rate. For example, the device can be a liquid pump with a pressure regulator. The device for introducing the solvent at a controlled rate can be connected to the device that is capable of providing a stream of gas in which the solvent can evaporate in any manner that allows for the distribution of the solvent. In one embodiment, the device that is capable of providing a stream of gas in which the solvent can evaporate comprises a nebulizer, which is used to mix gas and solvent and inject the resulting mixture into the device in a dispersed spray. In this embodiment, the solvent is injected into the nebulizer by a device for introducing the solvent at a controlled rate, and the solvent is mixed with a steam of gas and injected into the device that is capable of providing a stream of gas in which the solvent can evaporate. As the stream of gas and solvent proceeds through the device, the solvent evaporates, leaving dispersed particles of oil in the stream of gas. The particles of oil then pass through the light and form reflected light, which is detected. In this embodiment, the solvent introduced into the device that is capable of providing a stream of gas in which the solvent can evaporate will comprise a generally uniform concentration of oil, and the resulting signals produced by the light detector will change from a zero reading, to a maximum reading, and then back to a zero reading over time.

In another embodiment, a continuous volume of a second solvent can be provided to the device that is capable of providing a stream of gas in which the solvent can evaporate. In this embodiment, the solvent with the oil content is introduced into the second solvent while the second solvent is being constantly provided. In this manner, the signals produced by the light detector will change in intensity more gradually, and can accurately be charted, with the oil content represented as a peak. All of the components described herein can be used for the various components in this embodiment.

In addition, a conventional high-performance liquid chromatography (HPLC) device can be used as the device that can regulate the volume or pressure of a fluid. In this embodiment, in the mobile phase of the HPLC device is a second solvent, which includes, without limitation, any of the solvents mentioned herein, and which can be the same as or different than the solvent with extracted oil. In a preferred embodiment, the second solvent comprises isopropanol and hexane. In another preferred embodiment, the second solvent comprises 10% isopropanol and 90% hexane. Any HPLC device that is capable of supplying solvent to the device that is capable of providing a stream of gas in which the solvent can evaporate can be used. Examples of suitable HPLC devices include a Hewlett-Packard 1090 with a Micra NPS, 33×4.6 millimeter, 1.5 micron plus Guard Column. In this embodiment, the second solvent can be provided continuously.

Before addition of the solvent with the extracted oil to the second solvent, the light detector will not detect any reflected light, because the second solvent evaporates prior to reaching the light. The solvent with the extracted oil is then added to the flow of the second solvent, and is carried into either the HPLC column or directly to the device that is capable of providing a stream of gas in which the solvent can evaporate. In either embodiment, the solvent with the extracted oil becomes dispersed in the second solvent prior to reaching the device that is capable of providing a stream of gas in which the solvent can evaporate.

Upon introduction into the device that is capable of providing a stream of gas in which the solvent can evaporate, both solvents evaporate, and the oil is carried toward the light and light detector in the stream of gas. Since the solvent with the extracted oil is dispersed in the second solvent, the light detector will signal an increase from the zero baseline of the evaporated second solvent alone to a peak of oil content, and then back to the baseline of the evaporated second solvent when the oil particles have completely passed the light detector.

The HPLC is used as a readily available device for introducing the solvent at a controlled rate, and is not used here to separate components in the mobile solvent phase. For embodiments incorporating a second, continuously supplied solvent, including embodiments using HPLC devices, preferred values for flow rates and temperatures include, without limitation, those described herein for embodiments using only one solvent. In a preferred embodiment, the volume of a solvent with extracted oil that is added to the continuous flow of the second solvent is between 0.5 and 50 microliters, more preferably between I and 25 microliters, and even more preferably between I and 10 microliters. Although the entire sample of solvent with extracted oil can be added to the second solvent, any portion of the solvent with extracted oil can be added to yield a result that is proportional to the fraction of the solvent with extracted oil that was originally added.

The oil content of the solvent is determined with a light and a light detector. The light can be any light that is capable of being reflected by oil particles. Any light source that produces such light can be used as the light source. Potential light sources include lasers and collimated lasers. In a preferred embodiment, the light source is a 7 milliwattt, 670 nanometer laser diode. The light source is disposed so as to direct light into the stream of gas. As used herein, "directing light into a stream of gas" means providing a light source so that light emanating from the light source travels into the stream of gas. As particles of oil pass through the light, the light is reflected. As used herein, "reflected light" is any light that strikes an oil particle and is redirected toward the light detector.

The light detector can be any device that is capable of detecting light and outputting a signal that can be associated with the amount of light detected. In a preferred embodiment the light detected is reflected light. As used herein, "detecting reflected light" means generating a signal in response to light that has been produced by the light source, has been reflected by the extracted oil, and has struck the light detector. Suitable light detectors include, without limitation, silicon photodiodes, photomultipliers, and photon counters. In a preferred embodiment, a photodetector, which is a silicon photodiode, is used as the light detector. The photodetector in this embodiment outputs a signal that is proportional to the amount of reflected light striking the detector. The photodetector is preferably disposed at an angle relative to the path of the light. In one embodiment, the angle between the line of the light and the light detector is between 45 degrees and 135 degrees, with the vertex of the angle in the center of the long axis of the stream of gas and each line in the angle lying in the same plane, which is perpendicular to the long axis of the stream of gas. The light source and the light detector can be disposed at any distance from the stream of gas that allows for sufficient formation of reflected light and sufficient detection of that reflected light.

In order to associate the signals from a light detector with a quantity of oil, calibrations are performed with the methods of the present invention using a known amount of oil in a solvent. As used herein, "determining the oil content based on the reflected light" means using known calibration values of oil content and reflected light to determine oil content. Any volume of oil can be used to calibrate a device described herein, and in a preferred embodiment, an oil volume approximating the predicted oil content of a sample is used for calibration. Light detector signals for known oil concentrations, for example 0.1 to 3.5 milligrams per milliliter, can be used to create a model for correlating actual oil levels with light detector signals produced by a sample with unknown oil content.

The signals produced by the light detector can be sent to a device that is capable of storing or displaying the signal data. In one embodiment, a chromatograph is used to plot the amount of reflected light over time. In alternative embodiments, the signal data can be sent to data storage devices, computers, or a monitor. Once a plot of reflected light over time is produced, standard calculations can be used to determine the oil content as represented by the area under a peak on the curve of the plot.

The methods of the present invention are ideally suited to use in high throughput screening of seeds for oil content. The fast extraction time of the methods are suitable for an automated system using microtiter plates. In a preferred embodiment, the total time for extraction and determination of oil content of a sample is less than 10 minutes, more preferably less than 8 minutes, and even more preferably less than 6.5 minutes. In another preferred embodiment, relative oil content of samples is determined and extraction and determination of oil content is done in less than five minutes, preferably less than 3 minutes, and even more preferably in less than 1.5 minutes.

Methods of the present invention can be used in a breeding program to select plants or seeds having a desired trait. In one aspect, the present invention provides a method for selecting a seed having an enhanced oil content, comprising: extracting oil from a seed using a solvent; evaporating the solvent in a stream of gas to form oil particles; directing light into the stream of gas and the oil particles, thereby forming reflected light; detecting the reflected light; determining the oil content based on the reflected light; and, selecting a seed with a similar genetic background to the seed based on the oil content. In another aspect the present invention provides a method of introgressing a trait into a plant comprising: extracting oil from a seed using a solvent; evaporating the solvent in a stream of gas to form oil particles; directing light into the stream of gas and the oil particles, thereby forming reflected light; detecting the reflected light; determining the oil content based on the reflected light; selecting a seed with a similar genetic background to the seed based on the oil content; growing a fertile plant from the related seed; and, utilizing the fertile plant as either a female parent or a male parent in a cross with a second plant.

The methods of introgression and selection of the present invention can be used in combination with any breeding methodology, and can be used to select a single generation or to select multiple generations. The choice of breeding method depends on the mode of plant reproduction, the heritability of the trait(s) being improved, and the type of cultivar used commercially (e.g., $F_1$ hybrid cultivar, pureline cultivar, etc). Selected, non-limiting approaches for breeding the plants of the present invention are set forth below. A breeding program can be enhanced using marker assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability etc. will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred embodiment a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates for new commercial cultivars; those still deficient in traits may be used as parents to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated selfing and selection, producing many new genetic combinations.

The development of new soybean cultivars entails the development and selection of soybean varieties, the crossing of these varieties and selection of superior hybrid crosses. The hybrid seed can be produced by manual crosses between selected male-fertile parents or by using male sterility systems. Hybrids are selected for certain single gene traits such as pod color, flower color, seed yield, pubescence color or herbicide resistance which indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Pedigree breeding is used commonly for the improvement of self-pollinating crops. Two parents who possess favorable, complementary traits are crossed to produce an $F_1$. An $F_2$ population is produced by selfing one or several $F_1$'s. Selection of the best individuals in the best families is selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The single-seed descent procedure refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, soybean breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seed of a population each generation of inbreeding.

Descriptions of other breeding methods that are commonly used for different traits and crops can be found in one of several reference books (e.g. Fehr, *Principles of Cultivar Development* Vol. 1, pp. 2–3 (1987)), the entirety of which is herein incorporated by reference).

FIG. 1 provides one embodiment of a system that is capable of performing the methods of the present invention, which is shown generally at 10. A device for introducing the solvent at a controlled rate 12 is coupled with a source of a second solvent 14. The device 12 pumps the second solvent at a controlled rate to a device that is capable of providing a stream of gas 16 in which the solvent can evaporate, which in this case comprises a nebulizer 18 and a heated drift tube 20. A gas supply 22 is coupled to the nebulizer 18. The second solvent and the gas are mixed in the nebulizer 18, which causes the formation of a disperse stream of solvent droplets 24 in the drift tub 20. A light source 26 and a light detector 28 are disposed at an angle θ in a plane that is perpendicular to the long axis 30 of the drift tube 20. In this example, θ is 90 degrees. The light detector 28 outputs a signal 32 that is proportional to the amount of reflected light striking the detector 28.

To allow the introduction of the solvent with the extracted oil into the flow of the second solvent, a port 34 can be placed within the input line 36, or within the device 12. Finally, the light detector 28 can be coupled to a chromatograph 38 in order to graphically display the results of analyses.

EXAMPLE 1

The detector is calibrated with known soybean oil concentrations of 0.1 to 3.5 milligrams of oil per milliliter of solvent. The results of this calibration are shown in FIG. 2. FIG. 2 is a plot of area under a peak in a chromatograph (Y-Axis) versus the amount of extracted oil in the solvent (X-Axis). A sample of soybean is ground using a Tecator Cyclotec 1093 Sample Mill (Fos Tecator, P.O. Box 70, S-26321 Hoeganaes, Sweden). Twenty milligrams of ground seed is added to a microcentrifuge tube. One milliliter of hexane is added to the tube, and the tube is agitated for five minutes on a rotating wheel at room temperature. The tube is then centrifuged in a microcentrifuge for five minutes. The supernatant is transferred to an HPLC autosampler vial and injected into an HPLC apparatus. Five microliters of hexane with extracted oil is added. The HPLC apparatus is a Hewlett-Packard 1090 with a Micra NPS, 33×4.6 millimeter, 1.5 micron plus Guard Column. The second solvent is 10%/90% isopranol/hexane, the flow rate is 0.5 milliliters per minute, the column temperature is 40 degrees Celsius, and the run time is 0.8 minutes. The solvent is nebulized in a Varex Evaporative light scattering detector with a drift tube at 115 degrees Celsius, an exit temperature of 55 degrees Celsius, and an attenuation of 1. The chromatograph produced by this procedure is shown in FIG. 3. In FIG. 3, the Y-axis represents milliabsorbance units, which are units of reflected light intensity that are proportional to the mass of oil passing by the light detector. The X-axis represents time, in minutes. As can be seen in FIG. 3, a base line of reflected light is established from time zero. From time zero until 0.5 minutes into the run, only the second solvent is passing by the light detector. At just after 0.5 minutes, the extracted oil begins to pass by the light detector. The extracted oil entirely passes the light detector by the 0.8 minute mark of the run. The area under the peak centered at 0.594 is proportional to the mass of oil that passed by the light detector. The computed area under the peak curve can be located on the calibration graph shown in FIG. 2 in order to determine the mass of the oil that passed by the light detector.

EXAMPLE 2

FIGS. 4–6 show the results of comparisons between the oil content of the present invention (light scattering, or LS) with the conventional technique of accelerated solvent extraction (ASE). The conditions for determination of oil content for LS are as in example 1, and ASE is performed using conventional practices. FIG. 4 shows the percent oil content as determined for both LS and ASE, as well as the ratio (LS/ASE) of the oil content as determined by each method for 12 different samples. As shown in FIG. 4, the ratios of oil content fall significantly between 0.80 and 0.90. FIG. 5 shows the same ratio of oil content for ten sorghum samples. Again, the ratios of oil content fall within a narrow range, significantly between about 0.60 and 0.65. FIG. 6 shows the same ratio of oil content for maize. In this case, the ratios of oil content fall significantly between 0.7 and 0.8.

EXAMPLE 3

FIG. 7 demonstrates the reproducibility of one embodiment of the method of the present invention. As shown in FIG. 7, the range of oil content determined for ten identical runs is between about 2.75 and 3.25 percent oil for the ten samples of maize. The oil content of the samples are determined as in example 1.

EXAMPLE 4

FIG. 8 is an overlayed chromatogram of three separate runs. The Y-axis and X-axis are milliabsorbance units and time, respectively. The three peaks shown represent the peaks produced by runs of one, two and three *Arabodopsis thaliana* seeds. Each of the three samples is extracted using 250 microliters of hexane. The second solvent is a 5/95 mixture of Isopentanol/hexane, and the solvent is dispensed into the drift tube at a rate of 1.0 milliliters per minute. Conditions are otherwise as above for example two. The three overlayed peaks show the exceptional sensitivity and lower detection level of the methods of the present invention. As seen in the plot, for each *Arabidopsis thaliana* seed included, the area under the peak increases equivalently.

The above-described invention provides methods of determining oil content of samples with a higher sensitivity and lower detection limit than conventional methods, and that are amenable to automation. The methods can be rapidly performed with readily available devices on a wide variety of seeds, plant tissue, and agricultural materials. Further, unlike ultraviolet detection techniques, the methods of the present invention are mass sensitive, which allows for absolute quantition of oil content.

The above description, drawings and examples are only illustrative of embodiments which achieve the objects, features and advantages of the present invention. It is not intended that the present invention be limited to the illustrative embodiments.

What is claimed is:

1. A method for determining oil content of a seed comprising the steps of:

extracting oil from a seed using a solvent;

evaporating said solvent in a stream of gas to form oil particles;

directing light into said stream of gas and said oil particles, thereby forming reflected light from the oil particles;

detecting said reflected light; and, determining said oil content based on said reflected light.

2. The method of claim 1, wherein said seed has a mass of less than 100 micrograms.

3. The method of claim 1, wherein said seed has a mass of less than about 50 micrograms.

4. The method of claim 1, wherein said seed has a mass of less than about 25 micrograms.

5. The method of claim 1, wherein said solvent comprises an organic solvent.

6. The method of claim 1, wherein said solvent comprises a nonpolar solvent.

7. The method of claim 1, wherein said solvent is selected from the group consisting of hexane, petroleum ether, alcohol, decane, and acetonitrile.

8. The method of claim 1, wherein 0.5 to 50 mL of said solvent is used.

9. The method of claim 1, wherein 1 to 3 mL of said solvent is used.

10. The method of claim 1, wherein said step of evaporating is performed in an evaporative light scattering detector.

11. The method of claim 1, wherein said stream of gas comprises nitrogen.

12. The method of claim 1, further including the step of introducing said solvent into said stream of gas at a rate between 0.3 and 5 milliliters per minute.

13. The method of claim 1, wherein said light is laser light.

14. The method of claim 1, wherein said step of detecting said reflected light is performed with a silicon photodiode.

15. The method of claim 1, further including the step of heating said stream of gas.

16. The method of claim 1, further comprising the step of separating said seed from said solvent after said step of extracting.

17. The method of claim 16, wherein said step of separating is performed by centrifugation.

18. The method of claim 1, further comprising the step of introducing said solvent into a second solvent prior to said step of evaporating.

19. The method of claim 1, wherein said method is performed in less than 6.5 minutes.

20. The method of claim 1, wherein said method is performed in less than 1.5 minutes.

21. The method of claim 1, wherein said seed is maize.

22. The method of claim 1, wherein said seed is soybean.

23. The method of claim 1, wherein said seed is rapeseed.

24. A method for determining oil content of a sample comprising the steps of:
   extracting oil from a sample using a solvent;
   separating said solvent from said sample;
   evaporating said solvent in a stream of gas to form oil particles;
   directing light into said stream of gas and said oil particles, thereby forming reflected light from the oil particles;
   detecting said reflected light; and,
   determining said oil content based on said reflected light.

25. The method of claim 24, further comprising the step of introducing said solvent into a second solvent prior to said step of evaporating.

26. The method of claim 24, wherein said step of separating is performed by centrifugation.

27. A method for determining oil content of an agricultural product comprising the steps of:
   disrupting said agricultural product to produce ground product;
   extracting oil from said ground product using a solvent;
   evaporating said solvent in a stream of gas to form oil particles;
   directing light into said stream of gas and said oil particles, thereby forming reflected light from the oil particles;
   detecting said reflected light;
   determining said oil content based on said reflected light.

28. The method of claim 27, further comprising the step of introducing said solvent into a second solvent prior to said step of evaporating.

29. The method of claim 27, wherein said step of disrupting comprises the step of grinding.

30. A method for determining oil amount within a solvent/oil mixture, comprising the steps of:
   evaporating said solvent/oil mixture in a stream of gas to form oil particles;
   directing light into said stream of gas and said oil particles, thereby forming reflected light from the oil particles;
   detecting said reflected light; and,
   determining said oil amount based on said reflected light.

31. A method for determining oil amount within a solvent/oil mixture, comprising the steps of:
   introducing said solvent/oil mixture into a solvent carrier to form a processing solvent;
   evaporating said processing solvent in a stream of gas to form oil particles;
   directing light into said stream of gas and said oil particles, thereby forming reflected light from the oil particles;
   detecting said reflected light; and,
   determining said oil amount based on said reflected light.

32. A method for selecting a seed having an enhanced oil content, comprising the steps of:
   extracting oil from a seed using a solvent;
   evaporating said solvent in a stream of gas to form oil particles;
   directing light into said stream of gas and said oil particles, thereby forming reflected light from the oil particles;
   detecting said reflected light;
   determining oil content of the seed based on said reflected light; and,
   selecting a seed with a similar genetic background to said seed based on said determined oil content.

33. A method according to claim 32, further comprising the step of germinating said selected seed with a similar genetic background.

34. A method according to claim 32, further comprising the step of placing in a container said selected seed.

35. A method of introgressing a trait into a plant comprising the steps of:
   extracting oil from a seed using a solvent;
   evaporating said solvent in a stream of gas to form oil particles;
   directing light into said stream of gas and said oil particles, thereby forming reflected light from the oil particles;
   detecting said reflected light;
   determining said oil content based on said reflected light;
   selecting a seed with a similar genetic background to said seed based on said determined oil content;
   growing a fertile plant from said selected seed; and,
   utilizing said fertile plant as either a female parent or a male parent in a cross with a second plant.

36. A method according to claim 35, further comprising selecting a progeny of said cross having determined oil content.

37. A method according to claim 35, wherein said fertile plant is said male parent said cross.

38. A method according to claim 35, wherein said fertile plant is said female parent to said cross.

39. A method according to claim 35, wherein said plant is selected from the group consisting of alfalfa, apple, banana, barley, bean, broccoli, castorbean, citrus, clover, coconut, coffee, maize, cotton, cucumber, Douglas fir, Eucalyptus, Loblolly pine, linseed, melon, oat, olive, palm, pea, peanut, pepper, poplar, Radiata pine, rapeseed, rice, rye, sorghum, Southern pine, soybean, strawberry, sugarbeet, sugarcane, sunflower, sweetgum, tea, tobacco, tomato, turf, and wheat.

40. A method according to claim 35, wherein said plant is selected from the group consisting of cotton, maize, soybean, rapeseed, rice, and wheat.

41. A method according to claim 35, wherein said plant is maize.

42. A method according to claim 35, wherein said plant is soybean.

43. A method according to claim 35, wherein said plant is rapeseed.

44. A method for determining oil content of a seed comprising the steps of:

extracting oil from a seed using a solvent;

nebulizing said solvent containing said extracted oil under high pressure into a device capable of evaporating said solvent;

evaporating said solvent in a stream of gas in said device to form oil particles;

directing light into said stream of gas and said oil particles, thereby forming reflected light from the oil particles;

detecting said reflected light;

determining said oil content based on said reflected light.

45. A method for selecting a seed having an enhanced oil content, comprising the steps of:

a) extracting oil from a seed using a solvent;

b) evaporating said solvent in a stream of gas to form oil particles;

c) directing light into said stream of gas and said oil particles, thereby forming reflected light from the oil particles;

d) detecting said reflected light;

e) determining said oil content based on said reflected light;

f) repeating steps a) through e) one or more times, and, g) selecting one or more seeds based on said oil content.

46. A device, comprising:

a nebulizer that mixes a stream of gas with a mixture comprising a solvent and oil to create a dispersed spray;

a drift tube that receives the dispersed spray and within which the solvent evaporates leaving dispersed particles of the oil flowing in the stream of gas;

a source of emitted light that is directed into the drift tube and reflects off the flowing dispersed particles of oil;

a light detector operable to produce an output signal proportional to the amount of light reflected off the flowing dispersed particles of oil; and a signal processing functionality which determines an amount of oil present within the mixture from the output signal.

47. The device of claim 46 wherein the oil is extracted from at least one seed using the solvent.

48. The device of claim 46 further including a chromatograph connected to receive the output signal and produce a visual quantity indication of the flowing dispersed particles of oil.

49. The device of claim 46 wherein the source of light produces light capable of reflection off particles of oil.

50. The device of claim 49 wherein the produced light is laser light.

51. The device of claim 46 wherein the light detector comprises a photodetector.

52. The device of claim 46 wherein the solvent is selected from the group consisting of hexane, decane, petroleum ether, an alcohol, isopropanol and acetonitrile.

53. The device of claim 46 wherein the mixture comprises a supernatant.

54. The device of claim 46 wherein the stream of gas comprises a gas selected from the group consisting of an inert gas and a noble gas.

55. The device of claim 46 wherein the solvent comprises a first solvent and a second solvent.

56. The device of claim 55 wherein the first solvent is used to extract the oil from at least one seed.

57. The device of claim 56 wherein the first solvent is selected from the group consisting of hexane, decane, petroleum ether, an alcohol, isopropanol and acetonitrile, and the second solvent is selected from the group consisting of isopropanol, hexane, and mixtures thereof.

58. A device, comprising:

an input source of a mixture comprising a solvent and an unknown amount of oil; and an evaporative light scattering detection system that (a) receives the mixture from the input source, (b) forms the received mixture into a dispersed spray from which the solvent evaporates leaving dispersed particles of flowing oil that scatter light, (c) detects the scattered light; and (d) processes the detected scattered light to determine the unknown amount of oil which is present in the mixture.

59. The device of claim 58 wherein the evaporative light scattering detection system comprises:

a high-performance liquid chromatography (HPLC) device that evaporates the solvent from the mixture leaving the dispersed particles of flowing oil;

a source of emitted light that is reflected off the dispersed particles of flowing oil; and a light detector operable to produce an output signal responsive to detection of reflected light that indicates the presence of oil.

60. The device of claim 59 wherein the output signal is proportional to the amount of reflected light, the output signal being indicative of an amount of oil present within the mixture.

61. The device of claim 59 wherein the high-performance liquid chromatography (HPLC) device comprises:

a nebulizer that mixes a stream of gas with the mixture to create a dispersed spray; and a drift tube that receives the dispersed spray and within which the solvent evaporates leaving dispersed particles of the oil flowing in the stream of gas.

62. The device of claim 61 wherein the mixture comprises a supernatant.

63. The device of claim 59 further including a chromatograph connected to receive the output signal and produce a visual quantity indication of the dispersed particles of flowing oil.

64. The device of claim 59 wherein the source of light produces light capable of reflection off particles of oil.

65. The device of claim 64 wherein the produced light is laser light.

66. The device of claim 58 further including means for detecting an amount of scattered light, the detected amount of scattered light being indicative of an amount of oil present within the mixture.

67. The device of claim 58 wherein the solvent comprises a first solvent and a second solvent.

68. The device of claim 67 wherein the first solvent is used to extract the oil into the mixture from at least one seed.

69. The device of claim 67 wherein the first solvent is selected from the group consisting of hexane, decane, petroleum ether, an alcohol, isopropanol, and acetonitrile, and the second solvent is selected from the group consisting of isopropanol, hexane, and mixtures thereof.

70. A device, comprising:
a first input source of a mixture comprising a first solvent and an unknown quantity of oil;
a second input source of a second solvent including means for introducing the mixture into the second solvent;
a third input source of a stream of gas;
a nebulizer that mixes the stream of gas with the second solvent to create a dispersed spray containing first solvent droplets, second solvent droplets and included oil;
a drift tube that receives the dispersed spray and within which the first and second solvent droplets evaporate leaving drifting dispersed particles of the oil;
a source of emitted light that is directed into the drift tube and reflects off the drifting dispersed particles of oil;
a light detector operable to produce an output signal responsive to detection of reflected light; and
a signal processing functionality which processes the output signal to make a determination of the unknown amount of oil which is present in the mixture.

71. The device of claim 70 wherein the nebulizer and drift tube form a high-performance liquid chromatography (HPLC) device that evaporates the first and second solvents and releases the dispersed particles of oil from the mixture.

72. The device of claim 70 wherein the output signal is proportional to the amount of reflected light, the output signal being indicative of an amount of oil present within the mixture.

73. The device of claim 72 wherein the oil is extracted from the at least one seed using the first solvent.

74. The device of claim 72 further including a chromatograph connected to receive the output signal and produce a visual quantity indication of the dispersed particles of oil.

75. The device of claim 70 wherein the source of light produces light capable of reflection off particles of oil.

76. The device of claim 75 wherein the produced light is laser light.

77. The device of claim 70 wherein the light detector comprises a photodetector.

78. The device of claim 70 wherein the first solvent is selected from the group consisting of hexane, decane, petroleum ether, an alcohol, isopropanol, and acetonitrile, and the second solvent is selected from the group consisting of isopropanol, hexane, and mixtures thereof.

79. The device of claim 70 wherein the mixture comprises a supernatant.

80. The device of claim 70 wherein the stream of gas comprises a gas selected from the group consisting of an inert gas and a noble gas.

81. The method of claim 24 wherein the sample is selected from the group consisting of a seed, an agricultural product and a plant tissue.

* * * * *